United States Patent [19]
Durham et al.

[11] Patent Number: 5,514,145
[45] Date of Patent: May 7, 1996

[54] MAGNETIC POSITIONER ARRANGEMENT FOR LOCKING SCREWS FOR ORTHOPEDIC HARDWARE

[76] Inventors: Alfred A. Durham; Dallas P. Crickenberger, both of 2110 Carolina Ave., SW., Roanoke, Va. 24014

[21] Appl. No.: 237,922

[22] Filed: May 4, 1994

[51] Int. Cl.[6] .................................................. A61B 17/88
[52] U.S. Cl. ................... 606/96; 408/241 R; 408/115 R; 606/98
[58] Field of Search ................................ 606/62, 64, 67, 606/96, 98; 408/241 R, 16, 115 R, 115 B, 72 R, 72 B

[56] References Cited

U.S. PATENT DOCUMENTS

| | | |
|---|---|---|
| 3,961,632 | 6/1976 | Moossun . |
| 4,570,624 | 2/1986 | Wu . |
| 4,621,628 | 11/1986 | Brudermann . |
| 4,625,718 | 12/1986 | Olerud et al. . |
| 4,803,976 | 2/1989 | Frigg et al. . |
| 4,850,344 | 7/1989 | Olerud et al. . |
| 4,865,025 | 9/1989 | Buzzi et al. . |
| 4,877,019 | 10/1989 | Vives . |
| 4,881,535 | 11/1989 | Sohngen . |
| 4,901,711 | 2/1990 | Goble et al. ................ 606/98 |
| 4,917,111 | 4/1990 | Pennig et al. ................ 606/97 |
| 4,969,889 | 11/1990 | Greig ........................ 606/97 |
| 4,984,942 | 1/1991 | Holtz ..................... 408/241 R |
| 5,013,317 | 5/1991 | Cole et al. ................ 606/96 |
| 5,049,151 | 9/1991 | Durham et al. ............ 606/98 |

FOREIGN PATENT DOCUMENTS

| | | |
|---|---|---|
| 221356 | 4/1985 | Germany . |
| 668692 | 1/1989 | Switzerland . |
| 1447351 | 12/1988 | U.S.S.R. . |

OTHER PUBLICATIONS

Measurement of the Prostate in vivo with Magnetic Fields, William F. Chaltos, 12 Sep. 1963.

Primary Examiner—Tamara L. Graysay
Attorney, Agent, or Firm—Larson and Taylor

[57] ABSTRACT

A magnetic positioning system is provided for assisting in positioning a fastening element at a desired concealed internal location such as in a preformed opening in an interlocking nail in a long bone of a limb of a patient who has suffered a bone fracture. The arrangement includes: a first permanent ("target") magnet positioned at the internal location and a positioning device for a second permanent ("targeting") magnet. The positioning device comprises a hand-held drill and a magnetic aiming device mounted on the drill. The aiming device including a pivot member including the second magnet is disposed at one end thereof and having an axial bore. A mount for the pivot member permits three degrees of movement of the pivot member so as to enable the second magnet to align with the first magnet. The positioning device also includes a guide pin which is insertable into the axial bore and which is engaged by the drill chuck of the drill when the magnets are aligned. This enables the guide pin to be advanced by the drill along a path of travel in alignment with the first magnet and thus with the internal location. This path is ultimately followed by the fastening element.

20 Claims, 4 Drawing Sheets

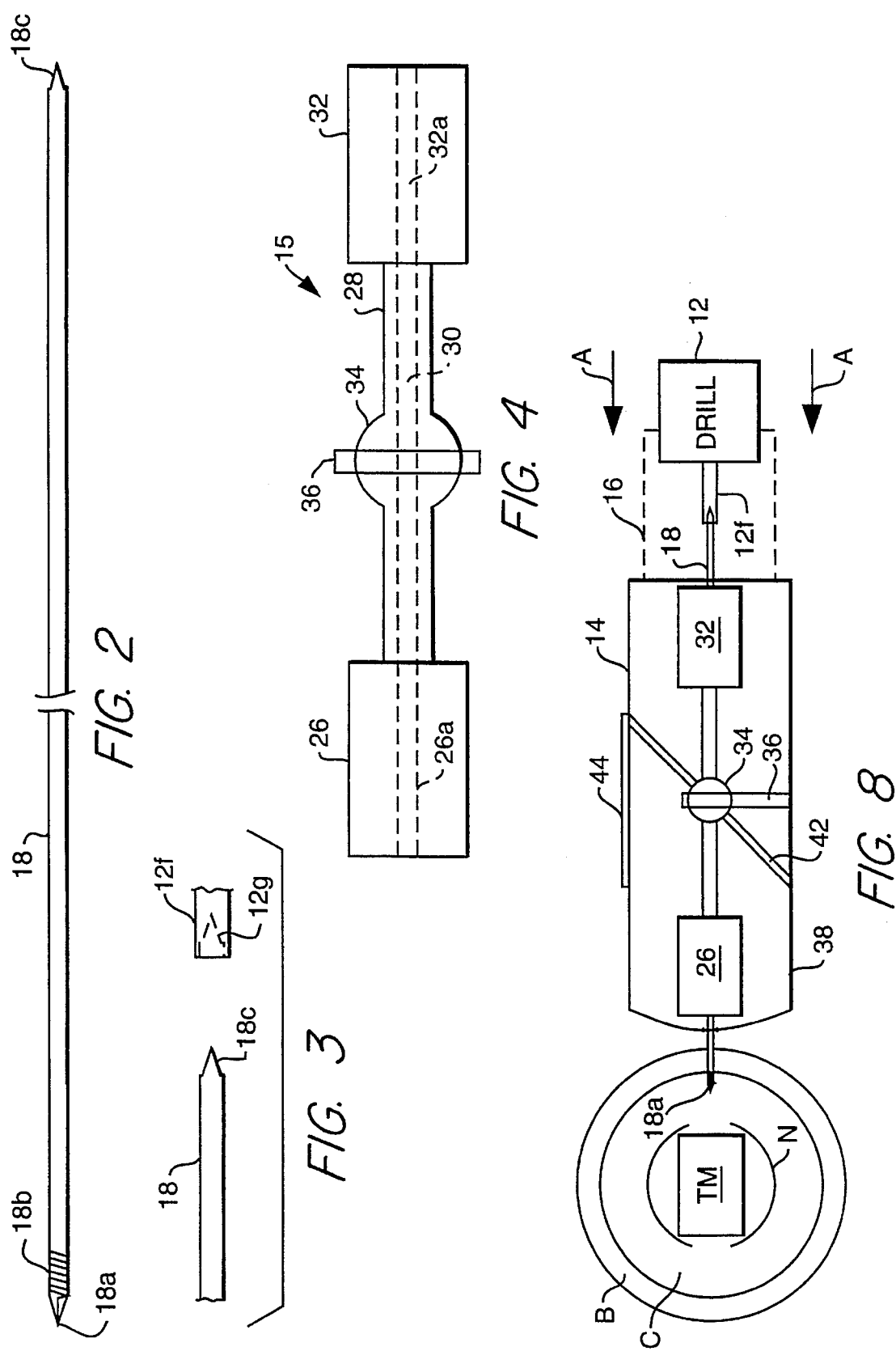

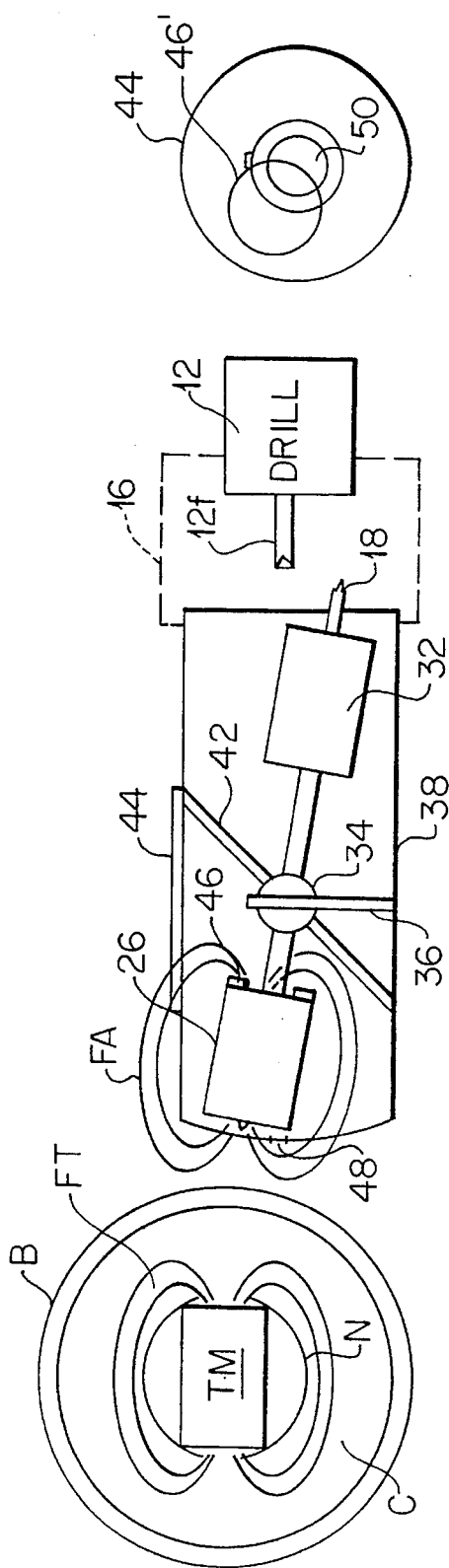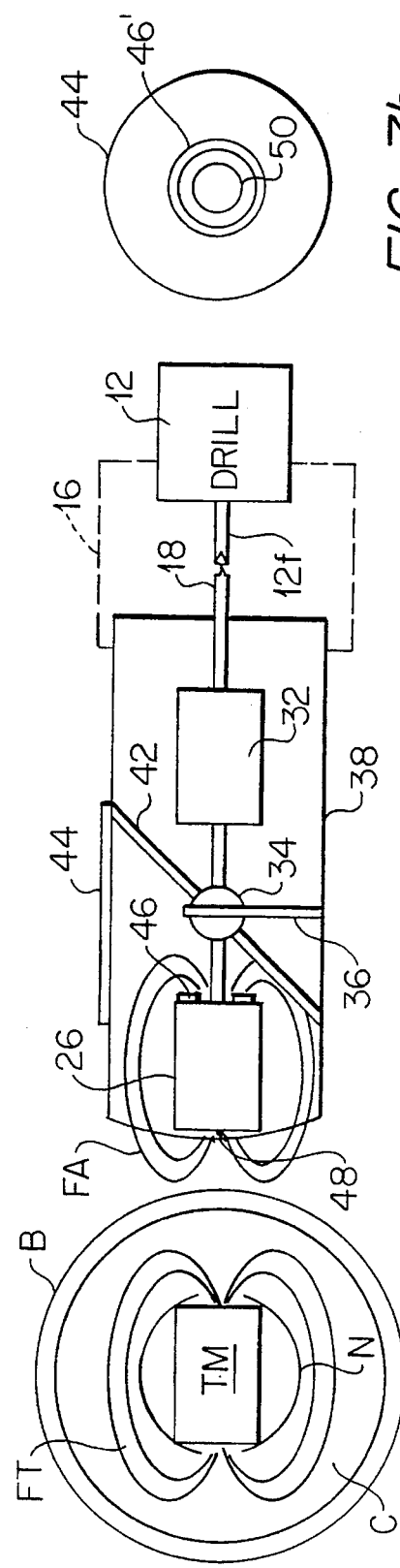

MAGNETIC POSITIONER ARRANGEMENT FOR LOCKING SCREWS FOR ORTHOPEDIC HARDWARE

FIELD OF THE INVENTION

The present invention relates to positioner devices and, more particularly, to arrangements for positioning locking screws or pins for orthopedic hardware such as interlocking rods. Although the invention is not limited to such an application, the invention specifically concerns a positioner or aiming (targeting) device for locking screw or pins for such orthopedic hardware which employs cooperating magnets to enable precise positioning of such screws or pins.

BACKGROUND OF THE INVENTION

Orthopedic hardware that is inserted in an intramedullary manner has become an increasingly useful aid in treating complex fractures of long bones, e.g., fractures of the femur or the tibia. In a typical application, an interlocking rod or bar, commonly referred to as a "nail," is inserted into a femur and transverse screws or pins, which are screwed or otherwise inserted from the outside of the limb or other body part through the bone and into distal and proximal transverse screw holes in the rod, are used to fix the rod in place in the bone.

The use of such locking screws to ensure that the rod is fixed firmly in position has extended the range of application of such orthopedic aids and appliances well beyond that of the original locking rods without such transverse screws. However, the problem of properly inserting the screws from the outside of the limb is a difficult one and a number of different approaches have been taken in an attempt to find a safe, effective and rapid way of inserting the locking screws and, in particular, the distal locking screws. In this regard, it is noted that such locking rods are long enough that the rods will bend when installed and thus locking or positioning devices which are centered based on a reference taken from the top of the rod have been ineffective in precisely locating the transverse screw holes. It will be understood that the locking screws or pins must be precisely located so that the load on the limb or other part of the body involved is transmitted through the screws or pins and associated interlocking rod, and not through the broken portions of the bone during healing of the bone.

One method that is capable of providing precise locating of the holes distally uses x-ray techniques, but long periods of x-ray exposure are required and the need to move the x-ray equipment in and out of position to check the screw or pin locations means that there is a risk of a loss of alignment each time the equipment is moved. As a consequence, the positioning of such locking screws or pins is typically the most time consuming and difficult portion of the overall rod implantation procedure.

Patents of interest in this field include U.S. Pat. Nos. 4,621,628 (Brudermann); 4,625,718 (Olerud et al.), and 4,570,624 (Wu). The Brudermann patent discloses an apparatus for locating transverse holes in the distal end of implanted locking "nails." The apparatus includes at least one magnet which generates an axially symmetrical field, in combination with a magnetic field detecting device or sensor having an axial field reception characteristic. In one embodiment, the magnetic field sensor is inserted into an implanted nail and the magnet, which is placed on the surface of the skin, is moved until axes of the magnetic field of the magnet and the sensor are aligned. More particularly, the sensor is connected to an external display device and alignment of the respective magnetic fields is indicated when a zero-point indication is provided on the display device. A second magnet can be used to increase the precision of the alignment process.

The other two patents are thought to be of more general interest, with the Olerud et al. patent disclosing an aiming apparatus using X-ray techniques for making holes or bores in the bone of a patient in registration with the holes or bores on an interlocking nail, and the Wu patent disclosing a mechanical technique for aligning surgical pins in parallel.

A further patent of particular interest here is our U.S. Pat. No. 5,049,151 (Durham et al.) relating to a method and apparatus for positioning the screws or pins of orthopedic hardware devices such as intramedullary rods, i.e., interlocking "nails." Broadly speaking, the Durham et al. patent involves the positioning of a first magnet at the location of a screw hole in the nail and then using an aiming device, comprising a second magnet which interacts with the first magnet, to locate the first magnet and hence enable a screw or pin to be placed in the screw hole in the nail to lock the nail in position. In one first embodiment, an insertion rod is used to position the first magnet at the level of the hole in the rod while in another embodiment, a solid nail is used and the magnet is removably disposed within the hole in the nail prior to implantation of the nail.

One very important advantage of the Durham et al. patent over the system disclosed in the Brudermann patent discussed hereinabove, is that the former eliminates the magnetic field sensor or detector and thus, the expensive auxiliary equipment (e.g., the display, signal processing unit and connecting circuitry) associated with the Brudermann system.

SUMMARY OF THE INVENTION

In accordance with the invention, a magnetic positioner is provided which is easier to use than prior art devices and which provides easier and more accurate alignment than is afforded by the prior art. In this regard, although the positioner arrangement of the Durham et al. patent discussed above possesses a number of important advantages, the present invention provides important additional advantages over the positioner arrangement disclosed in that patent, particularly in the areas of ease of use and ease and quality of the alignment.

In accordance with one aspect of the invention, a magnetic positioning system is provided for assisting in positioning a fastening element at a desired concealed internal location such as at a locking screw hole in an intramedullary rod in the bone of a patient, the arrangement comprising: a first permanent magnet adapted to be positioned at said internal location and providing a first directional magnetic field; and a positioning device; the positioning device comprising a hand-held drill including a drill chuck and a magnetic aiming device mounted on the drill, the aiming device including a pivot member including a second permanent magnet providing a second directional magnetic field at one end thereof and having an axial bore therethrough, and a mount for the pivot member which permits three degrees of movement of the pivot member, and thus of the second magnet, so as to enable the second magnet to align with the first magnet, the positioning device further comprising a guide pin insertable into the axial bore and adapted to be engaged by the drill chuck of said drill when the first and second magnets are aligned so as to enable the guide pin to be advanced by the drill along a path of travel in alignment with the first magnet and thus with the internal location.

In an advantageous embodiment, the aiming unit includes a protective cover. Preferably, the protective cover comprises a transparent plastic casing. The protective cover advantageously includes an opening in the distal end thereof through which the distal end of the guide pin can exit when the magnets are aligned. Preferably, the distal end of said cover is curved to accommodate pivoting movements of the second magnet. The pivot member of the aiming unit preferably includes a counterweight at the other end thereof. In an advantageous embodiment, the counterweight comprises a third magnet. The pivot member preferably includes a central shaft interconnecting the second magnet and the counterweight, and the mount preferably comprises a universal joint on which the shaft is supported. Preferably, the positioner device further comprises indicating means for indicating when the longitudinal axis of said second magnet is in alignment with the longitudinal axis of said aiming unit. Advantageously, the aiming unit includes a protective casing, and the indicating means includes a mirror system comprising a viewing port formed in the protective casing, and an inclined mirror, mounted within the protective casing and including an indicia on a surface thereof, for reflecting an image of at least a portion of the second magnet into said viewing port such that the relative positions of the image and the indicia provide an indication of the degree of alignment between the axes of the second magnet and the aiming unit. Advantageously, the second magnet includes a circle on the end thereof closest to the mirror and said indicia on the mirror comprises a further circle so that the relative concentricity of the two circles, as viewed through the viewing port, provides an indication of the relative alignment between said axes.

In a preferred embodiment, the guide pin includes a pointed or sharpened distal end in the nature of a trocar and an adjacent screw threaded portion. Advantageously, the guide pin further includes a shaped tip at the proximal end thereof of a shape (e.g., a spade tip) matched to the gripping surfaces of the drill chuck. Preferably, the drill includes means for enabling limited sliding movement of the drill chuck so as to enable limited advance of the guide pin relative to the aiming unit.

In accordance with a further aspect of the invention, a method is provided for positioning a fastening or locking element at a desired internal location concealed behind an external surface, the method comprising: locating a first permanent magnet having a first directional magnetic field at the desired internal location; preloading a guide pin into a positioning device comprising a magnetic aiming unit affixed to a hand-held drill, the aiming unit including a second pivotedly mounted permanent magnet having a second directional magnetic field; moving the positioning device along the external surface in the expected area of the internal location until the magnetic fields of the first and second magnets interact; using the drill to advance the guide pin into the external surface when the magnetic fields of the first and second magnets are in alignment; overreaming the guide pin to create an enlarged opening in the surface; removing the first magnet through the opening; and using the location of the guide pin as a guide, inserting a fastening or locking element into the opening.

In a preferred embodiment of this aspect of the invention wherein the internal location is within a bone in a limb of a patient, the magnet is located in an interlocking rod within the bone which is to be fixed in place in the bone, and the fastening or locking element comprises a locking screw or pin, the method further comprises screwing the locking screw or pin through one side of the bone, through the rod and into the other side of the bone so as to assist in locking the rod in place in the bone.

Other features and advantages of the invention will be set forth in, or apparent from, the following detailed description of preferred embodiments of the invention.

BRIEF DESCRIPTION OF THE DRAWINGS

FIG. 2 is a side elevational view, drawn to enlarged scale, of a guide pin used in the device of FIG. 1;

FIG. 3 is a side elevational view, drawn to a similar scale to that of FIG. 2, showing the manner of cooperation between the guide pin of FIG. 2 and a clutch sleeve of the device of FIG. 1;

FIG. 4 is a top plan view, drawn to an enlarged scale, and with parts omitted, of the internal aiming mechanism of the aiming unit of FIG. 1;

FIGS. 6a and 7a are schematic side elevational views showing two different orientations of the positioning device of FIG. 1 relative to the cross section of a bone containing an intramedullary nail, while FIGS. 6b and 7b are plan views of the viewing port of the device of FIG. 1 showing what an operator would see through that port for each respective orientations;

FIG. 8 is a side elevational view similar to FIG. 6a and 7a showing a further step in the use of the positioner device of FIG. 1;

DESCRIPTION OF THE PREFERRED EMBODIMENTS

Figure 1:
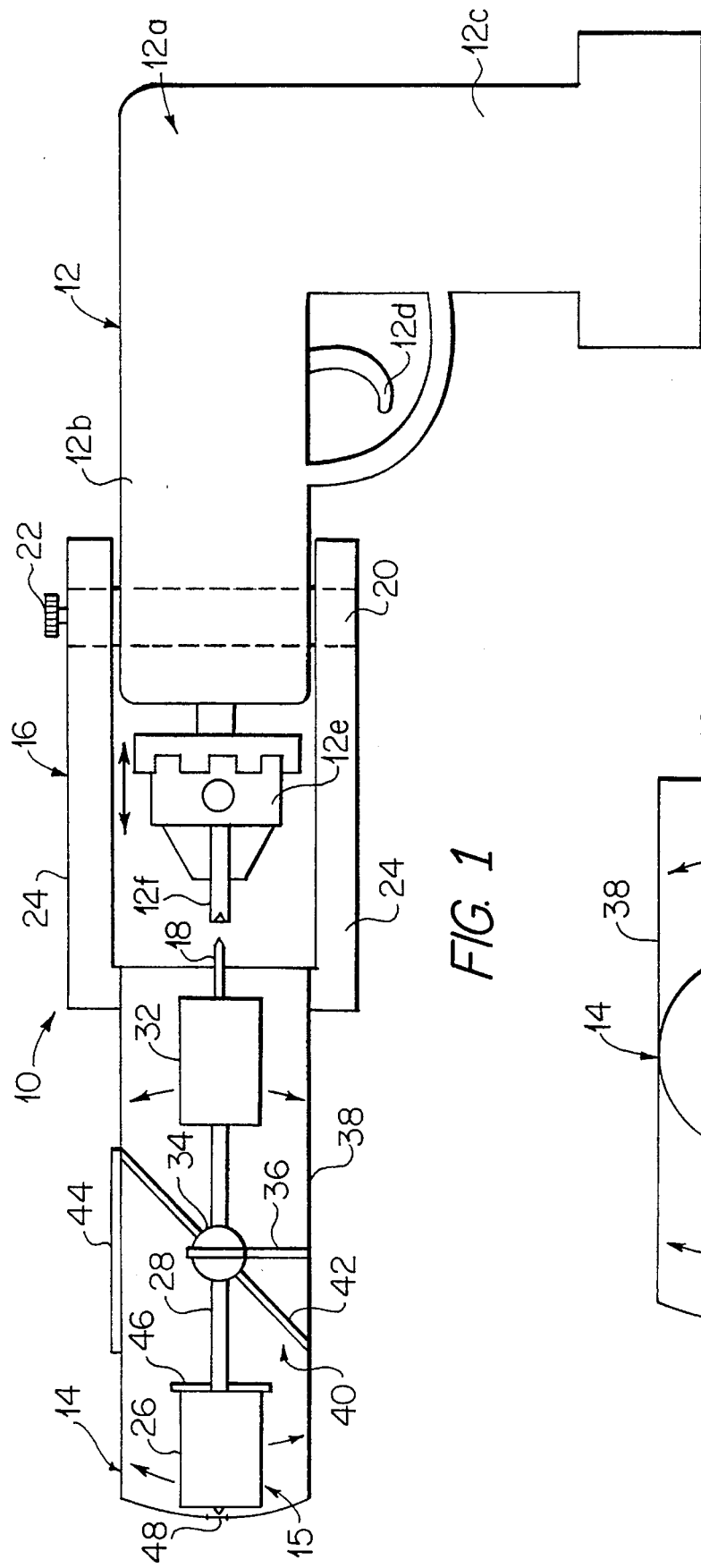
FIG. 1 is a schematic side elevational view of a positioner or aiming device constructed in accordance with a preferred embodiment of the invention.

Referring first to FIG. 1, a side elevational view of the overall aiming (targeting) or screw positioning device of the invention is shown. The device, which is generally denoted 10 basically comprises a drill 12, an aiming or targeting unit 14 and a support assembly 16 for mounting the aiming unit 14 on drill 12.

Drill 12 preferably comprises a conventional batterypowered, sterilizable orthopedic drill and includes a drill body 12a including a barrel portion 12b and a handle 12c, a trigger 12d and drive head 12e which rotates in response to the depression of trigger 12d by a user. Drive head 12e includes a sleeve 12f containing an internal chuck (not shown) which enables gripping of a guide pin, indicated at 18 in FIG. 1, so as to provide high speed rotation of the guide pin 18 by drill 12.

Guide pin 18 is shown in more detail in FIG. 2 and, as illustrated includes, at one end thereof, a sharpened trocar tip 18a with screw threading 18b and, at the other end, a flattened spade tip which is received in the hardened chuck of sleeve 12f. Guide pin 18 is made of a non-magnetic material and, in a specific non-limiting example, is approximately 1.6 mm in diameter. A set of such pins all of the same size and weight would be employed.

Referring to FIG. 3 the cooperating portions of guide pin 18 and mounting sleeve 12f are shown. As illustrated, sleeve 12f includes a recess 12g therein of a shape that matches the flattened spade tip 18c at the proximal end of pin 18.

Referring again to FIG. 1, the mounting assembly 16 can take a number of different forms and, in the illustrated embodiment, comprises a ring portion or ring 20 which fits around the barrel portion 12b of drill body 12a. Ring portion 20 is affixed or secured to barrel portion 12b by at least one set screw 22 or by other suitable fastener or fasteners, and a plurality of support arms 24 (two of which are shown in FIG. 1) extend outwardly from ring 20 to engage one end of aiming unit 14 and thus provide support therefor.

The basic internal elements of aiming unit 14 are shown to an enlarged scale in FIG. 4, these elements constituting the aiming or targeting mechanism 15 of aiming unit 14. As illustrated, the aiming mechanism 15 includes a first permanent magnet 26 mounted at one end of a hollow shaft 28 having an internal bore or cannulation 30 therein and a counterweight or counterbalance 32 mounted at the other end of shaft 28. Magnet 26 should be a strong magnet and in an advantageous embodiment comprises a neodymium iron boron magnet. Magnet 26 is predrilled so as to include a bore or cannulation 26a of the same diameter as, and in alignment with, bore or cannulation 30 in shaft 28 and of a slightly larger diameter than guide pin 18. Counterweight 32 includes a corresponding aligned bore 32a.

In an advantageous embodiment, rather than being a simple, shaped counterbalancing weight, counterweight 32 can comprise a second magnet, preferably one also made of neodymium iron boron. By using two such magnets, a "node effect" is produced where the individual magnets tend to increase the directionality of the magnetic field produced by the magnets and to hence increase to some extent the accuracy of the alignment process described below. If a magnet is used as counterweight 32, the drill chuck of drill 12 should be made of nonmagnetic materials so that the counterbalancing magnet 32 is not attracted to the drill 12 since this would obviously have an adverse effect on the aiming capabilities of unit 14.

Shaft 28 pivots around a central universal joint 34 which is advantageously of the "HEIM" (trademark for universal joint) type can be any assembly which allows shaft 28, and hence magnet 26, three degrees of freedom of movement. Some alternative mounting to a Heim joint or a gimbal include a tensioned small diameter wire for suspending the shaft 28 so as to enable free pivoting thereof, with the support wire being mounted in suitable, e.g., circular, yoke. Further, a rubber or plastic membrane could also be used for this purpose. Other approaches include pivoting of the aiming mechanism 15 in a thin layer of a confined liquid so as to provide flotation and hence pivoting of the mechanism.

A mounting or support bracket 36 is used to support the universal joint 34 within a protective casing 38 (see FIGS. 1 and 5) preferably made of a transparent lightweight material such as a lightweight plastic. The base of bracket 36 is affixed to casing 38 as shown in FIG. 1. It will be understood that different mounts of various configurations can be used to serve this purpose and that different mounts could also be used with alternative embodiments of the universal joint described above. Casing or housing 38 supports the aiming mechanism 15 formed by magnet 26, universal joint 34, and other components described above, in approximate axial alignment with the front portion of drill 12 so that when properly aligned there is only one collinear axis along which pin 18 can engage the clutch mechanism of sleeve 12f.

Figure 5:
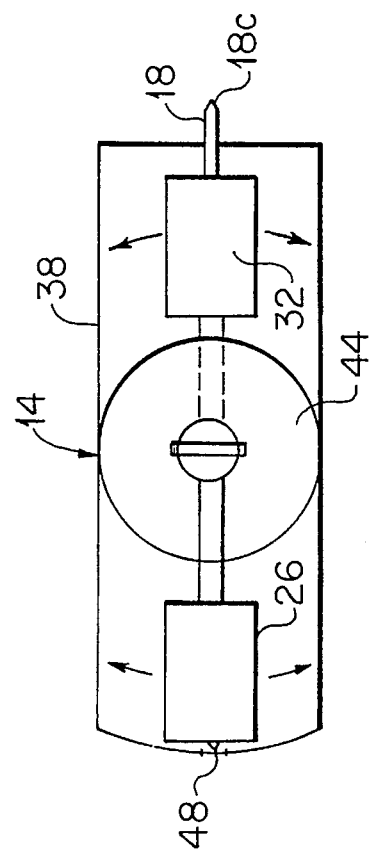
FIG. 5 is a top plan view of the aiming unit of FIG. 1.

As is also shown in FIGS. 1 and 5, a mirror assembly 40 is provided which includes a mirror 42 which is arranged at a 45° angle and which projects an image of magnet 26 onto or through a circular shaped viewing screen or viewing port 44 provided at the top of casing 38. Preferably, the targeting magnet 26 includes a small ring 46 of colored plastic or the like (see FIG. 1) and mirror would include a similar colored ring (not shown in FIG. 1) on the surface thereof so that when targeting magnet 26 is exactly aligned, the two colored circles are concentric as viewed through off-axis viewing port or screen 44, thereby indicating exact alignment of the pin 18 and drill 12.

A small central opening 48 is provided in casing 38 at the distal end thereof and is only lined up with the distal end of pin 18 when pin 18 is in alignment with clutch sleeve 12f. As illustrated, casing 38 is curved in this area so that magnetic aiming mechanism 15 is disposed very close to casing 38 but the casing 38 does not restrict the movement of aiming or targeting magnet 26. The small arrows shown in FIGS. 1 and 5 indicate possible directions of movement of the aiming device 15 around the universal joint 34 which as noted above, provides three degrees of freedom of movement.

Drill 12 is designed so that the drill head assembly 12e can slide forward a limited distance which is basically equal to difference between the length of pin 18 and the length of the aiming mechanism 15 formed by magnet 26, shaft 28, counterbalance 32, and the other components described above. This limitation on the longitudinal or sliding movement of drill head assembly 12 permits pin 18 to be drilled only through the proximal cortex of a bone and not down into or against the targeting magnets within a intramedullary rod within the bone.

Although the general operation of the device of FIGS. 1 to 5 should be evident from the foregoing description, the overall operation will now be considered in connection with FIGS. 6a and 6b and FIGS. 7a and 7b. In FIGS. 6a and 7a, the drill 12 and support assembly 16 are shown schematically since it is the operation of the aiming unit 14 that is of primary interest. FIGS. 6a and 7a each show, at the left side thereof, the intramedullary canal C of a long bone B in which is disposed an intramedullary rod or "nail" N having a target magnet TM located therein. It will be understood that the rod N is inserted into bone B longitudinally of canal C and that series of target magnets corresponding to TM are located along rod R, as is described, for example, in our U.S. Pat. No. 5,049,151, referred to above.

FIG. 6a shows the targeting device 10 approaching the target magnet TM which is located within rod or nail N and which produces lines of flux FT which can interact with the corresponding lines flux FA produced by aiming or targeting magnet 26. In the situation illustrated, the aiming or targeting unit 14 attached to drill 12 is misaligned with respect to the central axis of the magnetic field FT of the target magnet TM. Accordingly, as is illustrated schematically in FIG. 6b, an operator looking through the viewing port 44 in the protective casing or housing 38 would see a misalignment or lack of concentricity between the image 46' of the colored circle 46 provided on proximal end of magnet 26 and the colored circle on mirror 42. This colored circle was mentioned above and is denoted 50 in FIGS. 6b and 7b. In addition, the clutch sleeve 12f of drill 12 is out of alignment with the proximal end of guide pin 18 so that if drill 12 were to be advanced at this time, there would be no engagement with guide pin 18. Further, if guide pin 18 were to be advanced, pin 18 would encounter the internal wall of casing 38 and could not exit through the central opening 48 in casing 38.

Referring now to FIG. 7a, the positioning or targeting device 10 is shown in this figure in a position wherein the central magnetic axis of aiming magnet 26 is collinear with the central magnetic axis of target magnet TM by virtue of the alignment of the corresponding magnetic fields FA and FT. In particular, the magnets 26 and TM are collinear in the three planes. It will be appreciated that it is only in this position that guide pin 18 and drill clutch sleeve 12f are collinear, thereby allowing pin 18 to be advanced through the central opening 48 in casing 38. Further, this orientation is made apparent to an operator looking through the off-angle viewing port 44 in that, as shown in FIG. 7b, the operator will see that the colored circle 50 on mirror 42 and the image 46' of the colored circle on magnet 26 are concentrically aligned.

Referring to FIG. 8, a further step in the positioning process is shown wherein the clutch sleeve 12f of drill 12 is in engagement with guide pin 18 and the drill is advanced (in the direction of arrows A) so that the distal end 18a of guide pin 18 is drilled through the proximal cortex of bone B. A stop (not shown) is provided on drill 12 which is adjustable and which thus allows the depth of penetration of guide pin 18 to be controlled or limited such that pin 18 will stop short of, and cannot hit or otherwise contact, the target magnet TM.

Figure 9A:
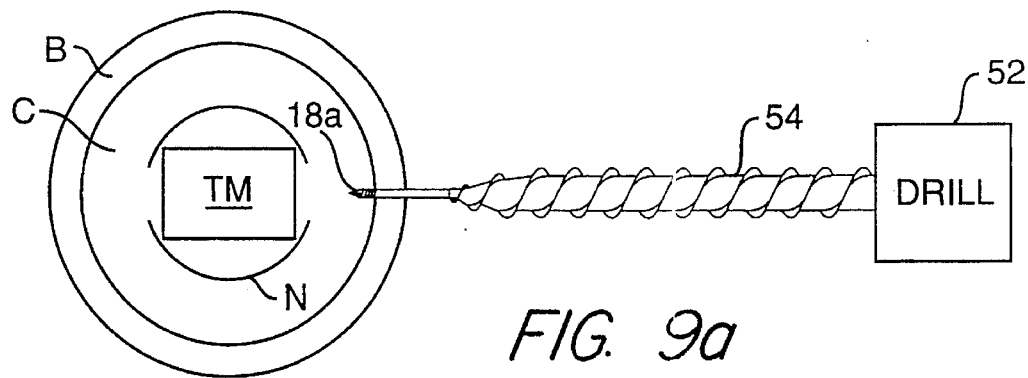
FIGS. 9a–9c are schematic side elevational views, including a cross section of the bone and intramedullary nail, showing a further step in the locking screw positioning process.
Figure 9B:
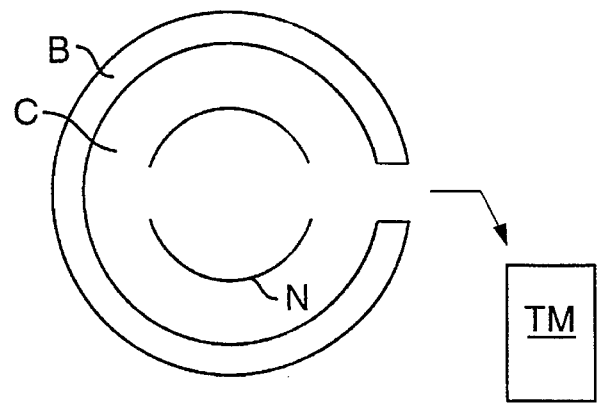
Figure 9C:
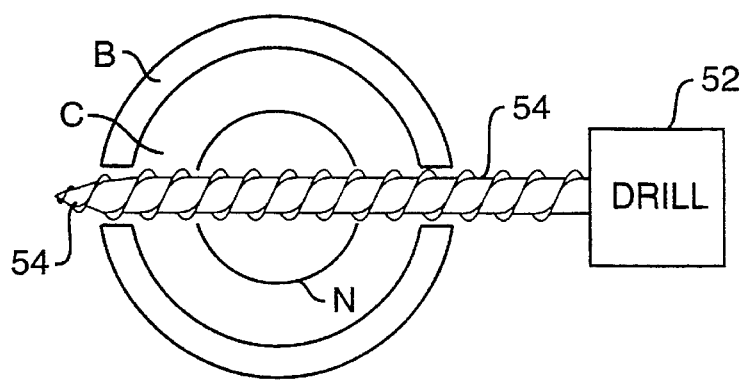

Once the central axis of the target magnet TM has been fixed by the location of the guide pin 18 in the proximal cortex of bone 3, the entire aiming device or assembly 10 including drill 12, is backed off of the pin 18, leaving the pin 18 behind. At this point, the target magnet TM is removed, as indicated in FIG. 9b, by, e.g., using one of the techniques disclosed in the above-mentioned U.S. Pat. No. 5,049,151. A further drill 52 is then used which includes a cannulated drill element 54. This drill element 54 is disposed so as to surround and overream guide 18 so that drill element 54 is ultimately inserted through the opening in nail N at which the target magnet TM was located prior to removal, as shown in FIG. 9a and then drilled completely through bone B, as shown in FIG. 9c.

It will be appreciated that the drilling operation described above would be carried out in stages and that, typically, drill element 54 would first be used to drill through the proximal cortex. The pin 18 and drill element 54 would then be removed and, for example, a cannula (not shown) inserted. A magnet on a rod (not shown) could then be inserted through the cannula to remove the target or guide magnet TM. In an advantageous embodiment, the target magnet TM could be screwed into the interlocking nail N and would include a hexagonal (hex-head) recess that would cooperate with matching hex-head projection on the removing magnet so as to permit the target magnet TM to be unscrewed from nail N. Alternatively, cooperating splines could also be used to mount the target magnet TM in the nail N. After the target magnet TM is removed, drill element 54 would then be used to complete the bore through the bone B.

Figure 10:
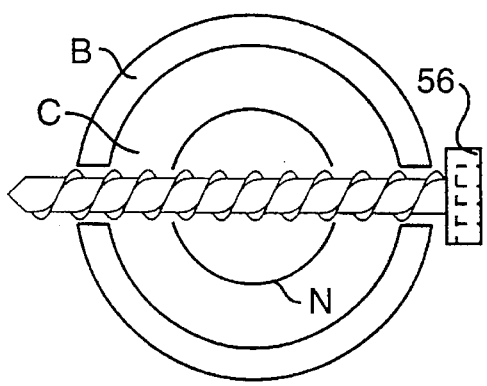
FIG. 10 is a schematic side elevational view similar to FIG. 9 showing the final step in the process.

In the next and final step, which is illustrated in FIG. 10, a screw fastener 56 is screwed into bone B through the nail N as to hold the nail N in place. Fastener 56 is, of course, screwed into the bore produced by drill element 54.

It will be appreciated from the foregoing that the present invention provides important advantages over the prior art, even including the positioner device of our U.S. Pat. No. 5,049,151. These advantages include improvements in areas of practicality and ease of use which accrue from the incorporation of features such as the associated hand-held drill 12 and the location of the aiming unit 14 on the front of the drill 12 in such a manner as to permit controlled penetration of the guide pin 18. This arrangement also allows the guide pin 18 to be advanced only when the magnetic axes of the targeting magnet C and the aiming or seeking magnet 26 are collinear. The mirror assembly 40, including the off-axis viewing port 44, also assists in enabling accurate alignment. In addition, encasement of the aiming mechanism 15 using casing 38 provides obvious advantages relating to protection of this mechanism, as well as the potential for percutaneous use of the device 10 in some patients by enabling compression of the soft tissues so as to reduce the distance that the drill element has to travel.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A magnetic positioning system for assisting in positioning a fastening element at a desired concealed internal location, said system comprising: a first permanent magnet adapted to be positioned at said internal location and providing a first directional magnetic field; and a positioning device; said positioning device comprising a hand-held drill including a drill chuck and a magnetic aiming device mounted on said drill, said aiming device including a pivot member including a second permanent magnet providing a second directional magnetic field at one end thereof and having an axial bore therethrough, and a mount for said pivot member which permits three degrees of movement of said pivot member and thus of said second magnet so as to enable said second magnet to align with said first magnet, said positioning device further comprising a guide pin insertable into said axial bore and adapted to be engaged by the drill chuck of said drill when said first and second magnets are aligned so as to enable the guide pin to be advanced by the drill along a path of travel in alignment with said first magnet and thus with said internal location.

2. The system as claimed in claim 1 wherein said aiming unit includes a protective cover.

3. The system as claimed in claim 2 wherein said protective cover comprises a transparent plastic casing.

4. The system as claimed in claim 2 wherein said protective cover includes an opening in the distal end thereof through which the distal end of said guide pin can exit when said magnets are aligned.

5. The system as claimed in claim 4 wherein said distal end of said cover is curved to accommodate pivoting movements of said second magnet.

6. The system as claimed in claim 1 wherein said pivot member of said aiming device includes a counterweight at the other end thereof.

7. The system as claimed in claim 6 wherein said counterweight comprises a third magnet.

8. The system as claimed in claim 6 wherein said pivot member includes a central shaft interconnecting said second magnet and said counterweight, and said mount comprises a universal joint on which said shaft is supported.

9. The system as claimed in claim 1 wherein said mount comprises a universal joint.

10. The system as claimed in claim 1 wherein said aiming device includes a fixed portion having a longitudinal axis and said second magnet has a longitudinal axis, and the positioning device further comprises indicating means for indicating when the longitudinal axis of said second magnet is in alignment with the longitudinal axis of said fixed portion of said aiming device.

11. The system as claimed claim 1 wherein said second magnet has a longitudinal axis and said aiming device includes a protective casing having a longitudinal axis, said positioning device further comprising indicating means including a mirror system comprising a viewing port formed in said protective casing, and an inclined mirror, mounted within said protective casing and including an indicia on a surface thereof, for reflecting an image of at least a portion of said second magnet into said viewing port such that the relative positions of the image and said indicia provide an indication of the degree of alignment between the longitudinal axis of said second magnet and the longitudinal axis of the protective casing of said aiming device.

12. The system as claimed in claim 11 wherein said second magnet includes a circle on the end thereof closest to said mirror and said indicia on said mirror comprises a further circle so that the relative concentricity of said circles as viewed through said viewing port provides an indication of the relative alignment between said axes.

13. The system as claimed in claim 1 wherein said guide pin includes a pointed distal end and an adjacent screw threaded portion.

14. The system as claimed in claim 13 wherein said drill chuck includes gripping surfaces and said guide pin further includes a shaped tip at the proximal end thereof of a shape matched to the gripping surfaces of said drill chuck.

15. The system as claimed in claim 1 wherein said drill includes means for enabling limited sliding movement of said drill chuck so as to enable limited advance of said guide pin relative to said aiming unit.

16. A magnetic positioning arrangement for assisting in the positioning of a locking element at an internal location behind an external surface that prevents the internal location from being determined visually, said arrangement comprising a first permanent magnet positioned at the internal location and providing a first directional magnetic field, a second permanent magnet providing a second directional magnetic field, a guide element, a hand-held drive tool for driving said guide element through the external surface in alignment with the internal location, and a targeting device, mounted on said drive tool and including means defining a pivot axis, for mounting said second magnet so that said second magnet can freely pivot about said pivot axis so as to enable the magnetic field of said second magnet to align with the magnetic field of the first magnet and thereby provide alignment of the second magnet with said internal location at which the locking element is to be positioned, said second magnet including an axial bore therethrough in which said guide element is received so that when said magnets are aligned, said guide element is positioned to be advanced by said drive tool so as to form a borehole in said external surface which is in alignment with said internal location and along the axis of which the locking element can be advanced when the guide element is removed.

17. The arrangement as claimed in claim 16 wherein said targeting device includes a counterweight, and a shaft interconnecting said second magnet and said counterweight, said means defining a pivot axis comprising a universal joint for mounting said shaft, said shaft and said counterweight including a bore in alignment with said bore in said second magnet, in which said guide element is received.

18. The arrangement as claimed in claim 17 further comprising optical means associated with said targeting device for indicating when said magnets are in alignment.

19. A method for positioning a locking element at a desired internal location concealed behind an external surface, said method comprising:

locating a first permanent magnet having a first directional magnetic field at the desired internal location;

preloading a guide pin into a positioning device comprising a magnetic aiming unit affixed to a hand-held drill, said aiming unit including a second pivotedly mounted permanent magnet having a second directional magnetic field;

moving said positioning device along said external surface in the expected area of said internal location until the magnetic fields of said first and second magnets interact;

using said drill to advance said guide pin into said external surface when the magnetic fields of said first and second magnets are in alignment;

overreaming said guide pin to create an enlarged opening in said surface;

removing the first magnet through said opening; and inserting a locking element into said opening.

20. The method as claimed in claim 19 wherein the internal location is within a bone in a limb of a patient, said first magnet is located in an interlocking rod within said bone which is to be fixed in place in said bone, and said locking element comprises a locking screw, and wherein the locating step includes placing said interlocking rod containing the first magnet within the bone, the inserting step includes inserting said locking screw into said opening and screwing said locking screw through one side of the bone, through said rod and into the other side of the bone.

\* \* \* \* \*